(12) United States Patent
Kim et al.

(10) Patent No.: US 9,314,278 B2
(45) Date of Patent: Apr. 19, 2016

(54) APPARATUS OF FIXING SPINOUS PROCESSES

(76) Inventors: Chang Kuk Kim, Yongin (KR); Soon Myoung Jung, Yongin (KR); Jin Oh Park, Yongin (KR)

(*) Notice: Subject to any disclaimer, the term of this patent is extended or adjusted under 35 U.S.C. 154(b) by 102 days.

(21) Appl. No.: 14/008,497

(22) PCT Filed: Jan. 18, 2012

(86) PCT No.: PCT/KR2012/000426
§ 371 (c)(1),
(2), (4) Date: Oct. 9, 2013

(87) PCT Pub. No.: WO2013/108939
PCT Pub. Date: Jul. 25, 2013

(65) Prior Publication Data
US 2014/0025114 A1    Jan. 23, 2014

(30) Foreign Application Priority Data
Jan. 17, 2012    (KR) .................... 10-2012-0005095

(51) Int. Cl.
*A61B 17/70* (2006.01)
(52) U.S. Cl.
CPC ......... *A61B 17/7067* (2013.01); *A61B 17/7062* (2013.01); *A61B 17/7068* (2013.01)
(58) Field of Classification Search
CPC ........... A61B 17/7053; A61B 17/7062; A61B 17/7064–17/7068; A61B 17/82
See application file for complete search history.

(56) References Cited

U.S. PATENT DOCUMENTS

| 7,922,745 | B2* | 4/2011 | Hestad et al. ............ 606/249 |
| 8,758,409 | B2* | 6/2014 | Hochschuler et al. ........ 606/249 |
| 8,968,365 | B2* | 3/2015 | Aschmann et al. ........... 606/248 |
| 2004/0117017 | A1* | 6/2004 | Pasquet et al. ........... 623/17.11 |
| 2005/0004674 | A1* | 1/2005 | Senegas et al. ........... 623/17.13 |
| 2007/0173818 | A1* | 7/2007 | Hestad et al. ................ 606/61 |
| 2008/0255668 | A1* | 10/2008 | Fallin ............... A61B 17/7065 623/17.16 |
| 2009/0292314 | A1* | 11/2009 | Mangione et al. ......... 606/249 |
| 2009/0292317 | A1* | 11/2009 | Belliard ................... 606/263 |
| 2009/0306716 | A1* | 12/2009 | Beger et al. ............... 606/249 |
| 2010/0100187 | A1* | 4/2010 | Le Couedic et al. ....... 623/17.16 |
| 2010/0185243 | A1* | 7/2010 | Pasquet et al. ............ 606/279 |

(Continued)

FOREIGN PATENT DOCUMENTS

KR    10-2006-0031385 A    4/2006
KR    10-20060116785 A    11/2006

(Continued)

*Primary Examiner* — Jacqueline Johanas
(74) *Attorney, Agent, or Firm* — Patent Office of Dr. Chung Park

(57) ABSTRACT

The present disclosure relates to an apparatus for curing spinal stenosis which is an abnormal narrowing of the spinal canal between spinous processes, more particularly, to an apparatus of fixing spinous processes which can prevent the narrowing or widening of the spinal canal between spinous processes along the motion of the spine so as to enhance spinal stabilization. The apparatus of fixing the spinous processes includes a spacer having at least predetermined portion inserted between spinous processes of two neighboring vertebrae to support the spinous processes so as to prevent narrowing of the spinous processes which is generated by spinal bending; and a clip provided to cover an outer surface of the spinous processes of the two neighboring vertebrae to prevent widening of a distance between the spinous processes generated by the spinal bending.

6 Claims, 7 Drawing Sheets

(56) References Cited

U.S. PATENT DOCUMENTS

| | | | |
|---|---|---|---|
| 2010/0204732 A1* | 8/2010 | Aschmann et al. | 606/249 |
| 2010/0256680 A1* | 10/2010 | Pasquet et al. | 606/249 |
| 2011/0071568 A1* | 3/2011 | Ginn et al. | 606/249 |
| 2011/0106163 A1* | 5/2011 | Hochschuler et al. | 606/264 |
| 2011/0144692 A1* | 6/2011 | Saladin et al. | 606/249 |
| 2011/0166605 A1* | 7/2011 | Hestad et al. | 606/279 |
| 2011/0295318 A1* | 12/2011 | Alamin et al. | 606/248 |
| 2012/0065683 A1* | 3/2012 | Kuo et al. | 606/248 |
| 2013/0012995 A1* | 1/2013 | Butterfield et al. | 606/248 |

FOREIGN PATENT DOCUMENTS

| | | |
|---|---|---|
| KR | 10-0850323 B1 | 8/2008 |
| KR | 10-2000-0069292 A | 6/2009 |

\* cited by examiner

APPARATUS OF FIXING SPINOUS PROCESSES

CROSS-REFERENCE TO PRIOR APPLICATIONS

This application is a national Stage Patent Application of PCT International Patent Application No. PCT/KR2012/000426, filed on Jan. 18, 2012 under 35 U.S.C. §371, which claims priority of Korean Patent Application No. 10-2012-0005095, filed on Jan. 17, 2012, which are all hereby incorporated by reference in their entirety.

BACKGROUND OF THE DISCLOSURE

1. Field of the Disclosure

The present disclosure relates to an apparatus for curing spinal stenosis which is an abnormal narrowing of the spinal canal between spinous processes, more particularly, to an apparatus of fixing spinous processes which can prevent the narrowing or widening of the spinal canal between spinous processes along the motion of the spine so as to enhance spinal stabilization.

2. Discussion of the Related Art

FIG. 1 is a sectional diagram of the human spine.

There are a predetermined number of spinous processes 3 along the spine and a vertebral body 7 in opposite to the process. The spinal nerve 1 is positioned in a space between the spinous processes 3 and the vertebral body 7. Between each two of the spinous processes are positioned an interspinous ligament 6 and a ligamentum flavum 5. There are a supraspinal ligament 4 and a skin 2 from the spinous processes 3 toward the human back.

As the human body is aging, degenerative change occurs in the spine and the spinous processes are narrowing as shown in a dotted line (A). In addition, the ligamentum flavum 5 is losing its elasticity to be projected forward as shown in a dotted line (B). Such change makes the spinous processes 3 or the ligamentum flavum 5 compress the spinal nerve 1 or a newrite (not shown) connected to the spinal nerve 1, which is called as "lumbar canal stenosis".

Therapy methods of the lumbar canal stenosis include drug treatment, physical treatment and surgery treatment. The surgery treatment is used unless the lumbar canal stenosis is cured by the other treatments. In the surgery, the bones and tissues compressing the spinal nerve are removed and a screw is used in immobilizing the spine in case the spine is instable.

However, the surgery treatment has to remove a wide range of the bone and tissues and patients usually results in losing a part of the spinal stabilization.

Such the surgery treatment requires general anesthesia and a long surgery time and a recovery time after the surgery. Accordingly, the elderly with weak immune systems frequently cannot have the surgery treatment.

Moreover, it disadvantageously happens that a satisfactory effect of the surgical operation cannot be made, because of surgical complications and other reasons. Also, the cost of the operation is disadvantageously high.

To overcome such the disadvantages mentioned above, methods of inserting a spine insert between two spinous processes 3 are proposed and a conventional related art is shown in FIG. 2.

As shown in FIG. 2, a conventional spine insert includes a spacer 10 inserted between two neighboring spinous processes 3 and a portion 11 for accommodating the two neighboring spinous processes 3. A groove is provided in the portion for accommodating the spinous processes 3 to couple the portion to a fixing strap. In addition, the spine insert may further include surface deformity portions 112 and 13 formed in surfaces adjacent to the spinous processes 3 to prevent the spinous processes 3 from separating there from.

In the related art, the surface deformity portions 12 and 13 might partially damage the spine while arranging the spacer 10 between the neighboring spinous processes 3.

Also, the spacer 10 is inserted between the two neighboring spinous processes 3 and the portion 11 for accommodating the spinous processes 3 is fixed by the strap after that. In this instance, the strap is wound around the spinous processes 3 several times to fix the spinous processes 3. That process has to be performed for an upper spinous process 2 and a lower spinous process 3 twice.

The conventional spine insert has the coupling structure which does not provide elasticity and it is likely for the spacer 10 to separate between the spinous processes 3 along the motion of the spine.

Accordingly, there are needs for a spinous process fixing apparatus having a simple structure which increases stiffness and stability of vertebrae and surgery easiness simultaneously, only to relieve the patients and doctors of burdens.

SUMMARY OF THE DISCLOSURE

An object of the present disclosure is to provide an apparatus of fixing spinous processes which may be inserted between neighboring vertebrae to enhance stiffness of a spinal segment and/or limit a vertical or horizontal motion of upper and lower vertebrae of the spine.

Another object of the present disclosure is to provide an apparatus of fixing spinous processes which reduce a surgery time by an increased surgery easiness so as to relieve a patient and a doctor of burdens.

To achieve these objects and other advantages and in accordance with the purpose of the invention, as embodied and broadly described herein, an apparatus of fixing spinous processes includes a spacer having at least predetermined portion inserted between spinous processes of two neighboring vertebrae to support the spinous processes so as to prevent narrowing of the spinous processes which is generated by spinal bending; and a clip provided to cover an outer surface of the spinous processes of the two neighboring vertebrae to prevent widening of a distance between the spinous processes generated by the spinal bending.

The spacer may include an inserting portion inserted between the spinous processes of the two neighboring vertebrae to support the spinous processes; and a coupling portion coupled to the clip.

The clip may include hook portions curved to cover outer surfaces of the spinous processes; a connecting portion which covers outer surfaces of the spinous processes, the hook portions facing each other; and a connecting portion which connects the clips with each other.

A predetermined portion corresponding to a space between the spinous processes is open and the space where the spacer is coupled to the clip may be formed.

The coupling portion of the spacer may be extended from a predetermined portion of the inserting portion inserted between the spinous processes of the neighboring vertebrae.

The coupling portion of the spacer may include a pair of first coupling grooves formed in both lateral surfaces facing ends of the hook portions to insert the ends of the hook portions therein, when the spacer is positioned in the open portion.

At least one projected portion may be formed in the connecting portion of the clip to provide an elastic tension to the hook portions.

The spacer may include a second coupling groove of which an inner diameter is larger than an entrance diameter to prevent a projected portion of the connecting portion of the clip from separating there from, when the projected portion of the connecting portion of the clip is coupled to the spacer, and a width of an end of the projected portion inserted in the second coupling groove may be larger than the entrance diameter of the second coupling groove, and a width of a portion outer to the second coupling groove may be smaller than the entrance diameter of the second coupling groove.

Here, to couple the spacer and the clip to each other more securely, the spacer may include a second coupling groove of which an inner diameter is larger than an entrance diameter to prevent a projected portion of the connecting portion of the clip from separating there from, when the projected portion of the connecting portion of the clip is coupled to the spacer, and a width of an end of the projected portion inserted in the second coupling groove is larger than the entrance diameter of the second coupling groove, and a width of a portion outer to the second coupling groove is smaller than the entrance diameter of the second coupling groove.

At least predetermined portion of the connecting portion provided in the clip may be curvedly projected toward the inserting portion of the spacer inserted between the spinous processes.

The coupling portion of the spacer may be extended from one end of the inserting portion inserted between spinous processes of two neighboring vertebrae and longer than the inserting portion in a longitudinal direction of the vertebrae.

In another aspect of the present disclosure, a method of installing an apparatus of fixing spinous processes includes a spacer inserting step configured to arrange an inserting portion of a spacer between spinous processes of two neighboring vertebrae; a clip coupling step configured to position a coupling portion of the spacer in an open portion of the clip, after arranging the inserting portion of the spacer, and to couple the clip to the spinous processes for hook portions of the clip to cover outer surfaces of the spinous processes; and a first coupling step configured to widen and insert both ends of the hook portions to the inserting portion of the spacer positioned in the open portion of the clip.

The method of installing the apparatus of fixing the spinous processes may further include a second coupling step configured to insertedly couple a projected portion of the connecting portion provided in the clip to a second connecting groove of the spacer.

In a further aspect of the present disclosure, an apparatus of fixing spinous processes includes a spacer provided between spinous processes of neighboring vertebrae, the spacer comprising spinous process inserting grooves formed in right and left sides of the spacer to insert a predetermined circumferential portion therein; and a clip comprising a first contact portion; a second contact portion; and a third contact portion.

The first contact portion may contact with the front surface of the spacer.

The second contact portion may extended from one end of the first contact portion, having at least predetermined portion which contacts with a rear surface of the spacer to form a first hole in which the spinous process is inserted.

The third contact portion may be extended from the other end of the first contact portion, having at least predetermined portion which contacts with the rear surface of the spacer and forming a second hole in which the spinous process is inserted.

A first inserting groove in which the first contact portion may be inserted is formed in a front surface of the spacer.

The length of the first contact portion is larger than the length of the first inserting groove.

A pair of second inserting grooves may be formed in a rear surface of the spacer to insert the second contact portion and the third contact portion therein.

The clip may include a bent portion formed between the first contact portion and the second contact portion and/or the first contact portion and the third contact portion.

An extended portion may be formed in a rear surface of the spacer to contact with the second contact portion and the third contact portion.

The extended portion may be formed of a flexible material which is curved toward the spinous processes when the extended portion contacts with the second contact and the third contact portion.

According to the embodiments of the present disclosure, there are following effects.

First of all, the apparatus of fixing the spinous processes may have a basic function of providing the flexible spacer between the two neighboring spinous processes, supporting them, only to prevent narrowing of the spinous processes.

Furthermore, the clip may be provided to cover neighboring spinous processes and the outer surfaces of the spacer inserted between the spinous processes, such that the widening between the spinous processes generated by the bending of the spine can be prevented and that the spacer may be fixed between the neighboring spinous processes stably.

Still further, the vertical or horizontal movement of the two neighboring spinous processes contacting with the spacer may be restricted by the spacer and the clip provided in the apparatus of fixing the spinous processes according to the exemplary embodiment of the present disclosure. Accordingly, the stabilization between the neighboring spinous processes may be maximized.

Still further, the open portion of the clip and the bent portion of the clip may allow the clip coupled to the outer surfaces of the spinous processes easily. Accordingly, the surgery convenience may be enhanced and the surgery time may be reduced. Also, a doctor and a patient may be relieved of burdens.

Still further, the elastic tension may be provided to the clip after the surgery and the possibilities of separation may be lowered.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

BRIEF DESCRIPTION OF THE DRAWINGS

The accompanying drawings, which are included to provide a further understanding of the disclosed subject matter and are incorporated in and constitute a part of this specification, illustrate exemplary embodiments of the disclosed subject matter, and together with the description serve to explain the principles of the disclosed subject matter.

DESCRIPTION OF SPECIFIC EMBODIMENTS

Figure 1:
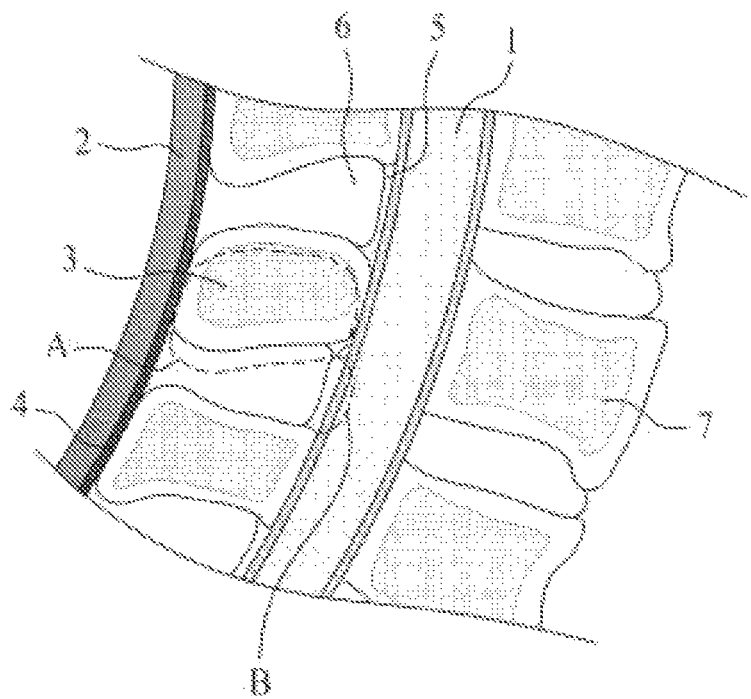
FIG. 1 is a sectional diagram of the human spine.
Figure 2:
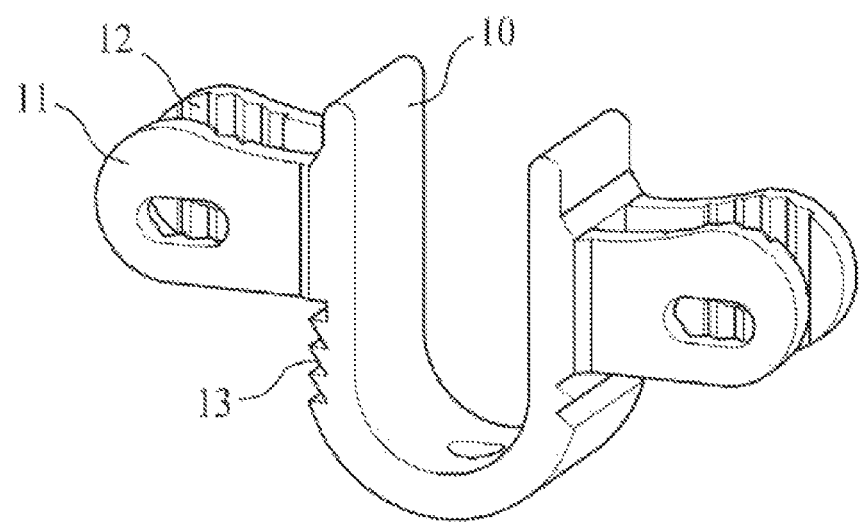
FIG. 2 is a diagram illustrating a related art.

Exemplary embodiments of the disclosed subject matter are described more fully hereinafter with reference to the accompanying drawings. The disclosed subject matter may, however, be embodied in many different forms and should not be construed as limited to the exemplary embodiments set forth herein. Rather, the exemplary embodiments are provided so that this disclosure is thorough and complete, and will convey the scope of the disclosed subject matter to those skilled in the art.

In the drawings, the size and relative sizes of layers and regions may be exaggerated for clarity. Like reference numerals in the drawings denote like elements.

It will be understood that when an element or layer is referred to as being "on", "connected to", or "coupled to" another element or layer, it can be directly on, connected, or coupled to the other element or layer or intervening elements or layers may be present. In contrast, when an element is referred to as being "directly on", "directly connected to", or "directly coupled to" another element or layer, there are no intervening elements or layers present. As used herein, the term "and/or" includes any and all combinations of one or more of the associated listed items. It may also be understood that for the purposes of this disclosure, "at least one of X, Y, and Z" can be construed as X only, Y only, Z only, or any combination of two or more items X, Y, and Z (e.g., XYZ, XYY, YZ, ZZ). It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another region, layer or section. Thus, a first element, component, region, layer, or section discussed below could be termed a second element, component, region, layer, or section without departing from the teachings of the present disclosure. The terminology used herein is for the purpose of describing exemplary embodiments only and is not intended to be limiting of the disclosed subject matter. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. An apparatus of fixing spinous processes according to one embodiment of the present disclosure shown in FIGS. 3, 4 and 5 may include a spacer and a clip.

The spacer may be inserted between spinal processes 3 of neighboring vertebrae to support the spinous processes 3. The spacer may include an inserting portion 200 and a coupling portion 210.

In description of embodiments, the vertebrae may include the cervical vertebrae, the thoracic vertebrae and the lumbar vertebrae.

Figure 6:
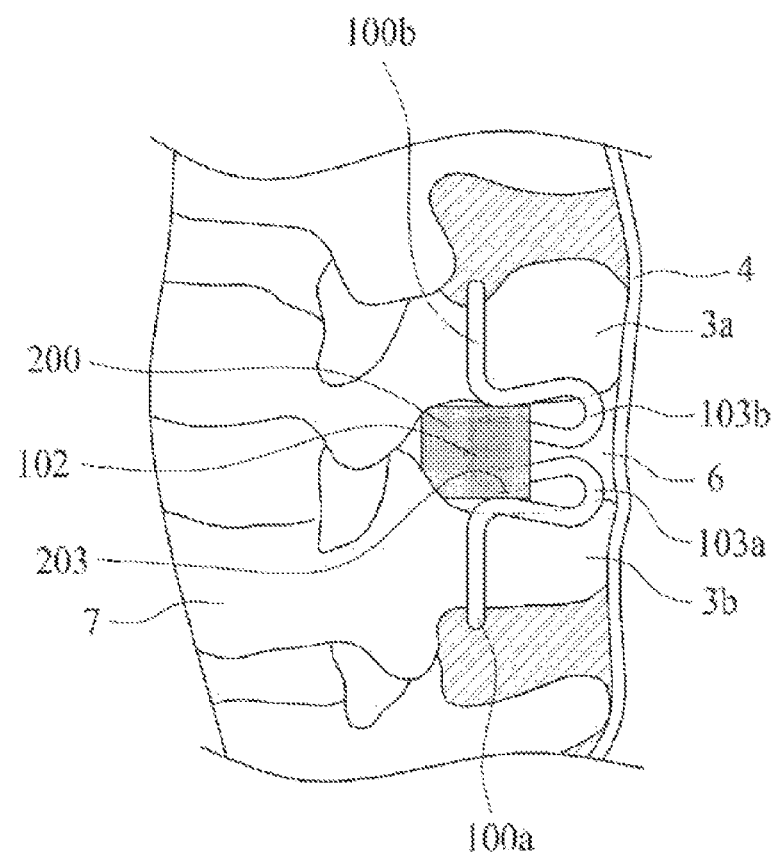
FIG. 6 is a side view illustrating a state where the apparatus of fixing the spinous processes according to one embodiment of the present disclosure is inserted in the human body.

As shown in FIG. 6, the inserting portion 200 may be inserted between spinous processes 3 of neighboring vertebrae to support the spinous processes 3, such that the spinous processes 3 may not be narrowed by the bending and pressing. The inserting portion 200 may be formed of a slightly elastic material which is harmless to human body (e.g., silicon and synthetic resin).

The coupling portion 201 of the spacer is a portion coupled to the clip and it is extended from the inserting portion 200 and projected outward with respect to the spinous processes 3, to be coupled to the clip.

An outward projected portion of the coupling portion 201 of the spacer may be longer than the width of the inserting portion 200 of the spacer in a longitudinal direction of the vertebrae.

The clip is coupled to outer portions of the spinous processes 3 of the two vertebrae to prevent the spinous processes 3 from getting farther by the bending of the vertebrae and simultaneously coupled to the spacer to fix the spacer between the spinous processes 3. The clip may be formed of a metallic material harmless to the human body (e.g., a shape memory alloy) and the embodiments of the present disclosure are not limited thereto. The metallic material may include various proper materials (e.g., synthetic resin).

Figure 3:
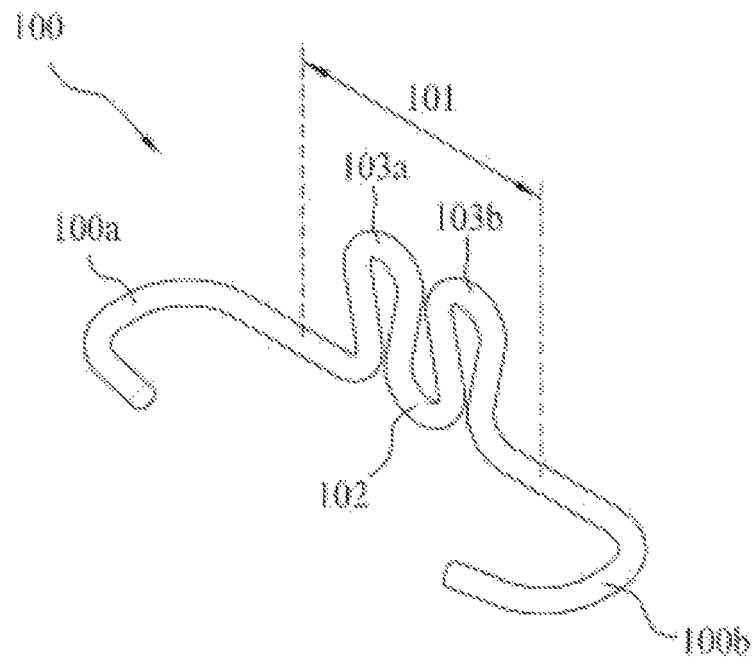
FIG. 3 is a perspective diagram illustrating a first embodiment of a clip provided in an apparatus of fixing spinous processes according to one embodiment of the present disclosure.
Figure 4:
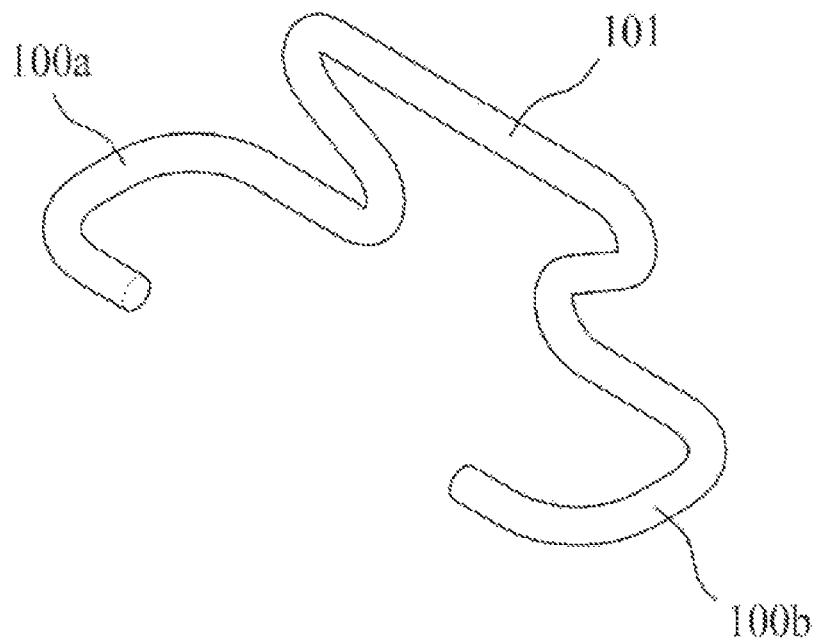
FIG. 4 is a perspective diagram of a clip provided in an apparatus of fixing spinous processes according to another embodiment of the present disclosure.

Such the clip may include a hook portion 100 and a connecting portion 101 as shown in FIGS. 3 and 4.

The hook portion may include gently curved portions in symmetry to cover the neighboring spinous processes 3.

The connecting portion 101 may be extended from the hook portion 100 to curved portions of the hook portions 100 with each other.

When the clip is coupled to the spinous processes 3, a portion of the clip corresponding to the space between the spinous processes 3 is open to form a space in which the clip and the spacer are coupled.

A first coupling groove may be formed in the spacer to couple the spacer to the clip.

At this time, the first coupling groove 202 may be formed in lateral surfaces of the spacer inserting portion 200 and the lateral surfaces may face ends of the hook portion 100 of the clip.

When the spacer is positioned in the open portion of the clip, an end of the hook unit 100 is insertedly coupled to the first coupling groove 202.

After the inserting portion 100 of the clip is inserted between the spinous processes 3 of the two neighboring vertebrae, the ends of the hook unit 100 formed in the clip are coupled to the first coupling groove 202.

As the spacer supports the spinous processes 3 in the space between the spinous processes 3 of the vertebrae and stenosis (A), in other words, narrowness between the spinous processes 3 of the neighboring vertebrae may be prevented and the clip coupled to the spacer may cover the outer surfaces of the spinous processes 3 to restrict the vertical or horizontal movement of upper and lower vertebrae.

The spacer and the clip are coupled to each other such that the apparatus of fixing the spinous processes from moving between the spinous processes 3 of the neighboring vertebrae.

Meanwhile, the clip may provide an elastic force to the connecting portion 101.

For that, the connecting portion 101 may include curvedly projected portions 102 and 103 as shown in FIGS. 3 and 4.

The exemplary embodiments are not limited thereto and the curvedly projected portions of the connecting portion 101 may be varied.

To describe this embodiment, the connecting portion may include a projected part with at least one of curved areas toward the inserting portion 200 positioned between ends of the hook portion 100 will be selected.

The connecting unit 101 may include one or more projected portions 102 curved toward the inserting portion 200 of the spacer. Accordingly, when a force is applied to the hook portions 100, the connecting portion 200 is elastically curved and an elastic tension to the hook portions 100.

Some of the other portions of the connecting portions are curved to the spinous processes 3 to be the projected portions 103. In other words, after the connecting portion 101 is curved and projected toward the spinous processes 3 in a wave shape, the connecting portion 101 is curved again and projected toward the inserting portion of the spacer inserted between the spinous processes.

Accordingly, an open portion of the clip is widened to couple the clip to the spacer easily and surgery convenience can be enhanced.

After the surgery, an elastic tension can be applied to the spacer and the clip and the possibilities of separation may be reduced.

Alternatively, the connecting portion 101 may be coupled to the spacer.

Figure 5:
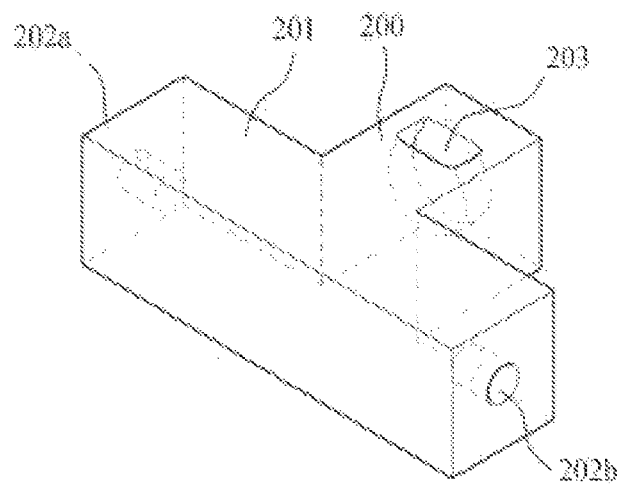
FIG. 5 is a perspective diagram of a spacer provided in the apparatus of fixing the spinous processes according to one embodiment of the present disclosure.

As shown in FIG. 5, a second coupling groove 203 may be formed in the inserting portion 200 of the spacer to be coupled to the curvedly projected portions 102 toward the spacer which is formed in the connecting portion 101.

As shown in FIG. 5, an inner diameter of the second coupling groove 203 may be larger than an entrance diameter of the second coupling groove 203. If a width of an end of the portion 102 curvedly projected toward the inserting portion 200, which is formed in the clip connecting portion 101 is formed larger than the entrance diameter, the coupling between the spacer and the clip can be performed more securely.

At this time, a predetermined portion of the clip connecting portion 101, which is outer to an entrance of the second coupling groove 203, without being inserted in the second coupling groove 203, is smaller than a width of a diameter of the entrance of the second coupling groove 203.

At this time, the position of the second coupling groove 203 may be variable in accordance with the shape of the connecting portion 101.

When the connecting portion 101 include a plurality of curvedly projected portions 102 and 103 shown in FIG. 3, the second coupling groove 203 of the inserting portion 200 may be formed in a front surface seen when the inserting portion 200 inserted between the two neighboring spinous processes 3 is seen behind the back shown in FIGS. 4, 5, 6, 7, 8, 9 and 10.

When the connecting portion 101 include only one curved projected portion 102 shown in FIG. 5, the second coupling groove 203 of the inserting portion 200 may be formed in a surface positioned in a direction where the inserting portion 200 is inserted between the spinous processes 3 as shown in FIG. 6.

However, when the connecting portion 101 does not include the curved portion 102 toward the inserting portion 200 of the spacer, the second coupling groove 203 for coupling the connecting portion 101 to the inserting portion 200 need not be formed.

Figure 7:
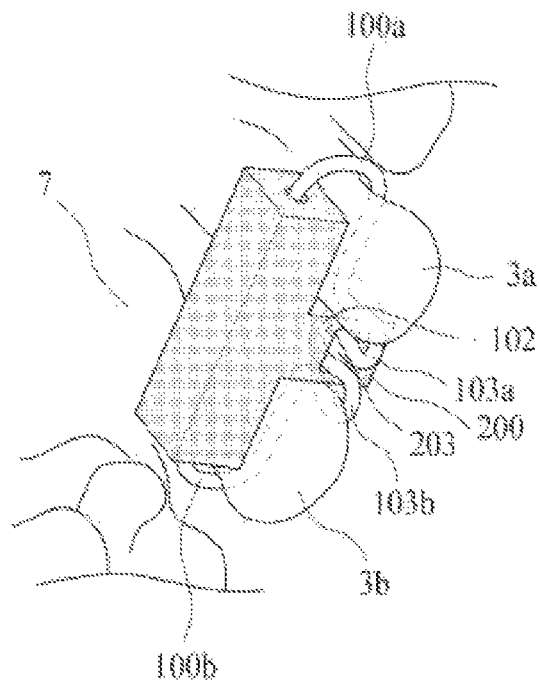
FIG. 7 is a perspective diagram illustrating the state where the apparatus of fixing the spinous processes according to one embodiment of the present disclosure is inserted in the human body.
Figure 8:
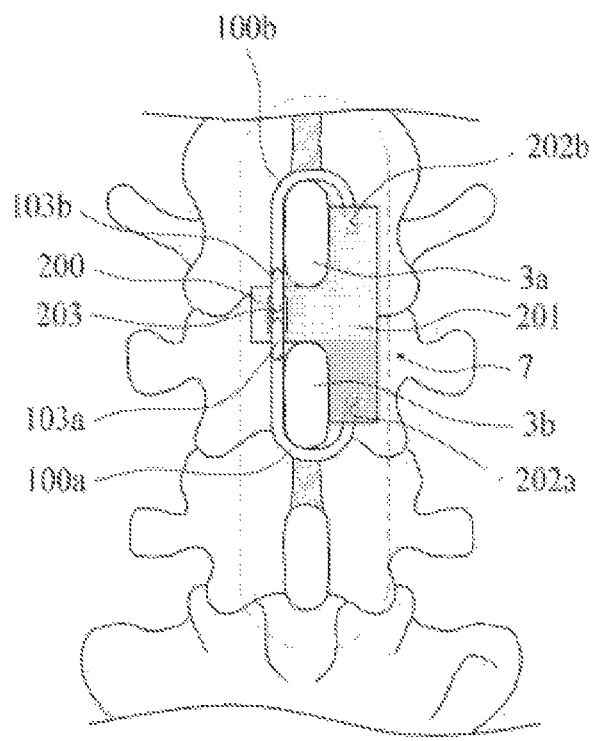
FIG. 8 is a front view illustrating a state where the apparatus of fixing the spinous processes according to one embodiment of the disclosure is inserted in the human body, seen from the back.

FIGS. 7 and 8 are diagrams illustrating the apparatus of fixing the spinous processes which is inserted in the human body.

In FIGS. 7 and 8, the spacer formed of an elastic material is arranged between two neighboring spinous processes 3 to prevent the spinous processes from narrowing (A).

The clip covers outer surfaces of the neighboring spinous processes 3, coupled to the spacer, such that the clip may prevent the spinous processes 3 from getting farther by the bending or pressing of the vertebrae. Simultaneously, the spacer may be fixed between the two spinous processes 3.

In addition, the coupling between the spacer and the clip may restrict vertical or horizontal movement of vertebrae above and below an intervertebral disc of the spine, such that the stabilization between neighboring vertebrae can be maximized.

A method for installing the apparatus of fixing the spinous processes according to one embodiment of the present disclosure will be described as follows.

The method for installing the apparatus of fixing the spinous processes according to this embodiment may include a spacer inserting, a clip coupling step and a first coupling step.

The spacer inserting step may position the inserting portion 200 of the spacer between the spinous processes 3 of two neighboring vertebrae.

The clip coupling step may arrange the inserting portion 200 of the spacer between the spinous processes 3 of the two neighboring vertebrae and position the coupling portion 201 of the spacer between open portions of the hook portions 100. Also, the clip coupling step may couple the clip to the spinous processes 3 for the hook portions 100 of the clip to cover outer surfaces of the spinous processes 3.

In the spacer inserting step, the coupling portion 201 of the spacer positioned between the spinous processes 3 of the two neighboring vertebrae may be positioned in the open portions of the clip.

The first coupling step may insert and couple both ends of the hook portions 100 in the first coupling groove 202 formed in and to the spacer positioned in the open portion of the clip.

Accordingly, the apparatus of fixing the spinous processes may be installed in the two neighboring spinous processes 3 and enhance spinal stabilization. Also, the apparatus of fixing the spinous processes may be fixed stably not to be srapted from the vertebrae.

When the clip is formed like the first embodiment, the second coupling groove 203 may be formed in the inserting portion 200 of the spacer. When the connecting portion 101 of the clip includes curved portion 102 toward the inserting portion 200 of the spacer, a second coupling step may be further provided.

The second coupling step may insert and couple the curvedly projected portion 102 toward the inserting portion 200 in and to the second coupling groove 203 of the spacer. Here, the curvedly projected portion 102 may be formed in the connecting portion of the clip.

Accordingly, a more stable spacer fixing effect and a higher spinal stabilization can be achieved.

Meanwhile, when the clip is formed similar to the other embodiments, the second coupling step need not.

Figure 9:
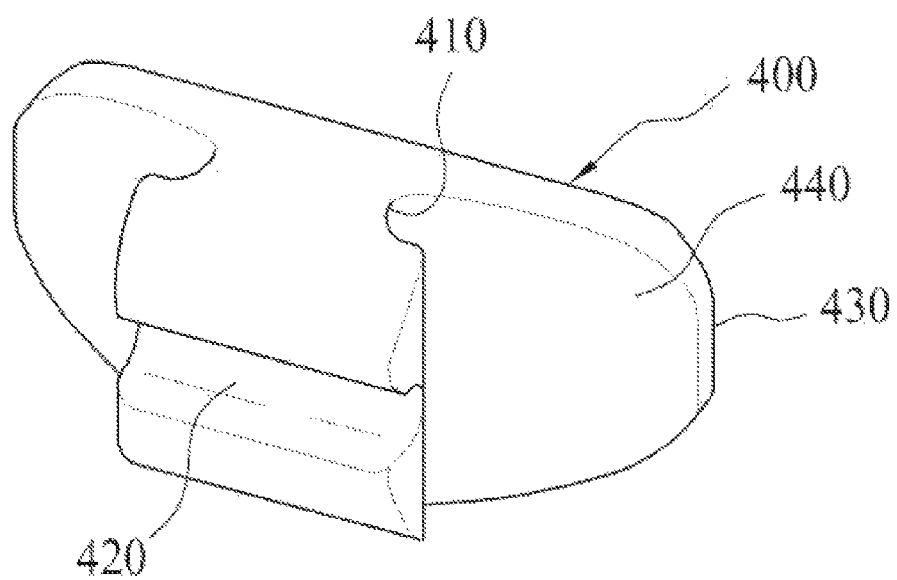
FIG. 9 is a perspective diagram of a clip provided in an apparatus of fixing spinous processes according to a further embodiment of the present disclosure.
Figure 10:
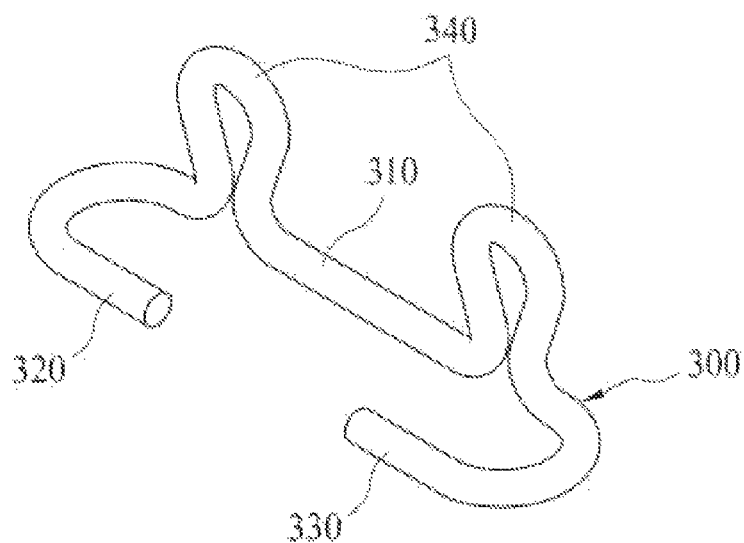
FIG. 10 is a perspective diagram of a spacer provided in the apparatus of fixing the spinous processes according to a further embodiment of the present disclosure.

FIG. 9 is a perspective diagram of a clip provided in an apparatus of fixing spinous processes according to a further embodiment of the present disclosure. FIG. 10 is a perspective diagram of a spacer provided in the apparatus of fixing the spinous processes according to a further embodiment of the present disclosure.

Referring to FIGS. 9 and 10, a configuration and a structure of an apparatus of fixing spinous processes according to another embodiment of the present disclosure will be described.

The apparatus of fixing the spinous processes according to the present disclosure is provided to cure spinal stenosis which is an abnormal narrowing of the spinal canal between spinous processes, more particularly, to an apparatus of fixing spinous processes which can prevent the narrowing or widening of the spinal canal between spinous processes along the motion of the spine so as to enhance spinal stabilization.

Such the apparatus of fixing the spinous processes may include a spacer 400 and a clip 300.

Figure 13:
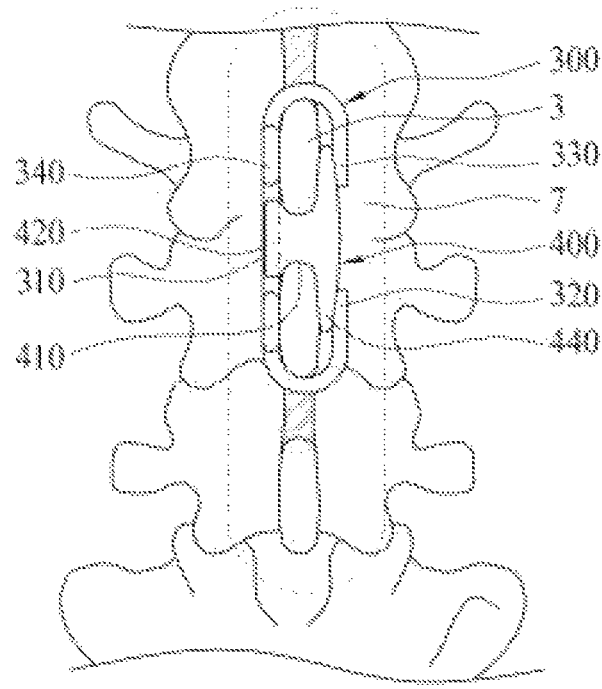
FIG. 13 is a front view illustrating a state where the apparatus of fixing the spinous processes according to a further embodiment of the disclosure is inserted in the human body, seen from the back.
Figure 14:
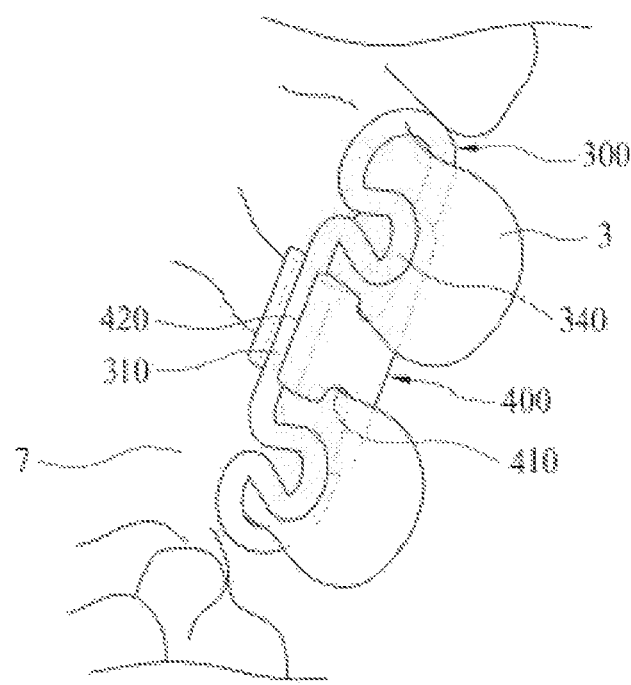
FIG. 14 is a perspective diagram illustrating a state where the apparatus of fixing the spinous processes according to a further embodiment of the disclosure is inserted in the human body.

The spacer 400 is inserted between two neighboring spinous processes 3 to support the spinous processes 3 inside and keeps a distance between the spinous processes 3 to present narrowing (stenosis) of the spinous processes 3 (see FIGS. 13 and 14). As shown in FIG. 9, a spinous process inserting groove 410 may be formed in right and left sides of the spacer 400 and predetermined portions of circumferences of the spinous processes 3 may be inserted in the spinous process inserting groove 410.

The spacer 400 may be formed of an elastic material which is harmless to the human body (e.g., silicon and synthetic resin) and it can absorb a shock generated along the motion of the spine.

The clip 300 may be provided to cover outer surfaces of the two neighboring spinous processes 3 and to prevent separation of the spacer 400 from the spinous processes 3 and simultaneously to prevent increase of a distance between the spinous processes 3. Also, the clip 300 may restrict vertical and horizontal movement of neighboring two vertebrae and maximize stabilization of the two neighboring vertebrae (see FIGS. 13 and 14).

As shown in FIG. 10, the clip 300 may include a first contact portion 310, a second contact portion 320 and a third contact portion 330.

Figure 11:
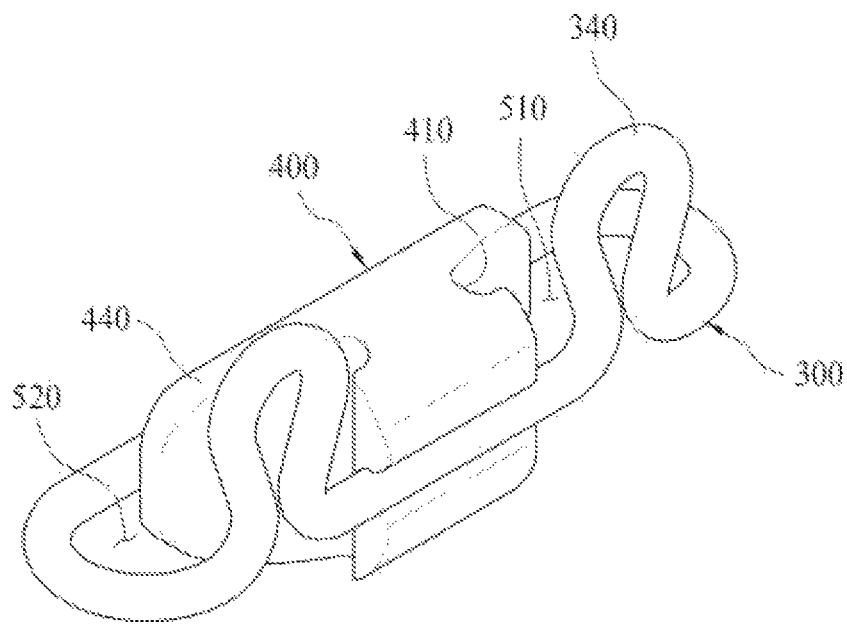
FIG. 11 is a perspective diagram illustrating a front surface of the apparatus of fixing the spinous processes according to a further embodiment of the present invention.
Figure 12:
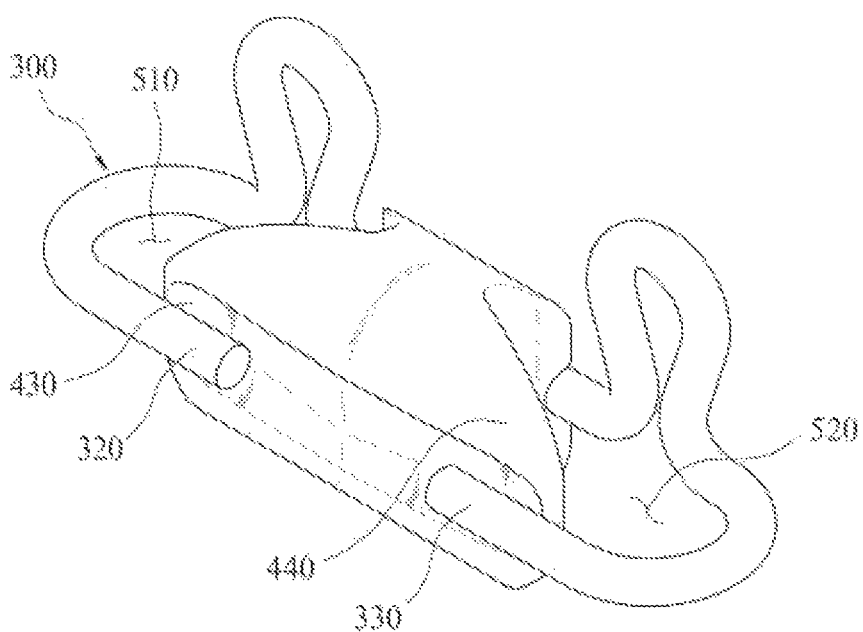
FIG. 12 is a perspective diagram illustrating a rear surface of the apparatus of fixing the spinous processes according to a further embodiment\t of the present invention.

FIG. 11 is a perspective diagram illustrating a front surface of the apparatus of fixing the spinous processes according to a further embodiment of the present invention. FIG. 12 is a perspective diagram illustrating a rear surface of the apparatus of fixing the spinous processes according to a further embodiment of the present invention.

As shown in FIG. 11, at least predetermined portion of the first contact portion 310 may contact with a front surface of the spacer 400.

The second contact portion 320 may be extended from one end of the first contact portion 310. As shown in FIG. 12, at least predetermined portion of the second contact portion 320 may contact with a rear surface of the spacer 400 and a first hole 510 may be formed in the second contact portion 320 to insert the spinous processes 3 therein.

The third contact portion 330 may be extended from the other end of the first contact portion 310. At least predetermined portion of the third contact portion 330 may contact with the rear surface of the spacer 400 and a second hole 520 may be formed in the third contact portion 330 to insert the spinous processes 3 therein.

At this time, an extended portion from the first contact portion 310 to the second contact portion 320 may be a U-shape configured to extend along the longitudinal direction of the patient's spine as shown in FIG. 13, bending like an outer cover for spinous processes 3. An extended portion from the first contact portion 310 to the third contact portion 330 may be a U-shape configured to extend along the longitudinal direction of the patient's spine as shown in FIG. 13, bending like an outer cover for the spinous processes 3.

The clip 300 may be formed of a metallic material which is harmless to the human body (e.g., a shape memory alloy). The clip 300 is formed from one monolithic body having a first and a second free end. The clip is a wire having a circular cross section as is shown in FIG. 10.). However, the material of the clip 300 may not be limited thereto and other various materials fitted to that condition (e.g., synthetic resin) may be used in forming the clip 300.

Meanwhile, as shown in FIG. 11, a first inserting groove 420 may be formed in a front surface of the spacer 400 to insert the first contact portion 310 therein. The length of the first contact portion 310 may be larger than the length of the first inserting groove 420.

Shapes of the first contact portion 310 and first inserting groove 420 may be various. However, in this embodiment, the first contact portion 310 may be linear-shaped, without the bent portion and the first inserting groove 420 may be also linear-shaped, corresponding to the first contact portion 310.

Accordingly, the first contact portion 310 may be guided by the first inserting groove 420 such that the spacer 400 and the clip 300 may be coupled to each other more smoothly and also that the apparatus of fixing the spinous processes may be applied to each of the spinous processes 3 more variously.

As shown in FIG. 12, the spacer 400 may include a pair of second inserting grooves 430 formed in the rear surface of the spacer 400. The second contact portion 320 and the third contact portion 330 which comprise the first and second free ends of the clip, respectively, may be inserted in the second inserting grooves 430, respectively, to couple the spacer 400 and the clip 300 to each other more stably.

At this time, the second inserting grooves 430 may be longer than the second contact portion 320 and the third contact portion 330. When the first contact portion 310 is longer than the first inserting groove 420, a predetermined space may be secured in which the first contact portion 310 guided by the first inserting groove 420 moves in a right or left direction.

A bent portion 340 may be formed at least one of between the first contact portion 310 and the second contact portion 320 formed in the clip 300 and between the first contact portion 310 and the third contact portion 330.

When the clip 300 is coupled to the spinous processes 300, a force is applied to the second contact portion 320 and the third contact portion 330 and an elastic tension is provided to the clip 300. Accordingly, the clip 300 may be coupled to the spinous processes 3 more smoothly and convenience of the surgery may be enhanced. The clip 300 may prevent the distance between the spinous processes 3 from getting farther along the movement of the spine, in a state wherein the clip 300 is coupled to the spinous processes 3, or it may be employed as buffer between the spinous processes 3. Moreover, as the elastic tension is applied to the clip 300 even after the surgery, the separation of the clip 300 and the spacer 400 generated from the movement of the spine may be prevented.

In the drawings of this embodiment, a pair of U-shaped bent portions 340 may be formed between the first contact portion 310 and the second contact portion 320 and between the first contact 310. The bent portion 340 may be projected toward the spinous processes 3 thereby extending along a direction normal to a longitudinal direction of a patient's spine as shown in FIG. 14. What is mentioned above, the bent portion 340 may be provided between the first contact portion 310 and the second contact portion 320 or the first contact portion 310 and the third contact portion 330. The shape of the bent portion 340 is not limited to what is shown in the drawing and any shapes capable of providing the elastic tension to the clip may be applied. For example, the bent portion 340 may be projected toward a vertebral body or bent in a different shape.

The spacer 400 may include an extended portion 440 formed in the rear surface thereof and the extended portion may contact with the second contact portion 320 and the third contact portion 330. The lengths of the second contact portion 320 and the third contact portions 330 may be adjusted in accordance with the length of the extended portion 440 variously. The extended portion 440 may be longitudinally formed in the rear surface of the spacer 400 to support the spacer 400 with respect to the spinous processes 3.

The extended portion 440 may be formed of a flexible material which can be curved toward the spinous processes 3 when contacting with the second contact portion 320 and the third contact portion 330. When the second contact portion 320 and the third contact portion 330 are coupled to the spacer 400, the extended portion 440 may be curved toward the spinous processes 3 to ease the coupling. Also, the extended portion 440 formed of the flexible material may be properly applied to individual spinous processes 3 having unique shapes, respectively.

FIG. 13 is a front view illustrating a state where the apparatus of fixing the spinous processes according to a further embodiment of the disclosure is inserted in the human body, seen from the back. FIG. 14 is a perspective diagram illustrating a state where the apparatus of fixing the spinous processes according to a further embodiment of the disclosure is inserted in the human body.

Referring to FIGS. 13 and 14, a brief method for coupling the apparatus of fixing the spinous processes according to this embodiment and effects are described as follows.

As shown in FIGS. 13 and 14, a spacer 400 may be inserted between two neighboring spinous processes 3 to position the pair of the spinous processes 3 in an inserting portion 410 of the spacer 400.

After a first contact portion 310 of a clip 300 is positioned in a first inserting groove 420, a second contact portion 320 and a third contact portion 330 are widened to insert the spinous processes 3 in a first hole 510 and a second hole 520.

Lastly, the second contact portion 320 and the third contact portion 330 are positioned in a second inserting groove 430 formed in a rear surface of the spacer 400.

According to the embodiments of the present disclosure, the apparatus of fixing the spinous processes according to this embodiment may have a simple coupling process between the spacer 400 and the clip 300 in a surgery and enhance surgery convenience. Accordingly, the surgery time may be reduced and burdens on a patient and a doctor in the surgery may be relieved. Also, the patient recovery time may be reduced.

Although embodiments have been described with reference to a number of illustrative embodiments thereof, it should be understood that numerous other modifications and embodiments can be devised by those skilled in the art that will fall within the spirit and scope of the principles of this disclosure.

More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An apparatus for fixing spinous processes comprising:
   a spacer including an insertion portion that is configured to be inserted between spinous processes of neighboring vertebrae, and has a first insertion groove and two extending portions; and
   a clip formed from one monolithic body having a first and a second free end, said clip comprising:
      a first contact portion that detachably engages in the first insertion groove;
      two bent portions extending from both ends of the first contact portion respectively, each said bent portion having a U-shape that is configured to extend along a direction normal to a longitudinal direction of a patient's spine;
      a second contact portion having a proximal end connected to a first one of the two bent portions, a distal end portion which comprises the first free end for contacting a first one of the two extending portions of the spacer, and a U-shape that is configured to extend along the longitudinal direction of the patient's spine to thereby form a first space for receiving a spinous process therein; and
      a third contact portion having a proximal end connected to a second one, of the two bent portions, a distal end portion which comprises the second free end for contacting a second one of the two extending portions of the spacer, and a U-shape that is configured to extend along the longitudinal direction of the patient's spine to thereby form a second space for receiving a spinous process therein.

2. The apparatus for fixing the spinous processes of claim 1, wherein a length of the first contact portion is larger than a length of the first insertion groove.

3. The apparatus for fixing the spinous processes of claim 1, wherein a pair of second insertion grooves is formed in the two extending portions of the spacer and configured to receive the distal end portions of the second and third contact portions therein.

4. The apparatus for fixing the spinous processes of claim 1, wherein the two extending portions of the spacer are formed of a flexible material and are bent toward the insertion portion of the spacer when the two extending portions contact the distal end portions of the second and third contact portions.

5. The apparatus for fixing the spinous processes of claim 1, wherein the clip is formed of a wire.

6. The apparatus for fixing the spinous processes of claim 5, wherein the wire has a circular cross section.

* * * * *